(12) United States Patent
McClellan, III

(10) Patent No.: US 9,138,327 B1
(45) Date of Patent: *Sep. 22, 2015

(54) PIVOTING INTERBODY VERTEBRAL SPACER

(76) Inventor: John W. McClellan, III, Omaha, NE (US)

( * ) Notice: Subject to any disclaimer, the term of this patent is extended or adjusted under 35 U.S.C. 154(b) by 545 days.

This patent is subject to a terminal disclaimer.

(21) Appl. No.: 13/401,972

(22) Filed: Feb. 22, 2012

Related U.S. Application Data

(60) Continuation of application No. 13/189,939, filed on Jul. 25, 2011, now abandoned, which is a division of application No. 11/533,782, filed on Sep. 21, 2006, now Pat. No. 8,025,697.

(51) Int. Cl.
*A61F 2/44* (2006.01)
(52) U.S. Cl.
CPC .............. *A61F 2/4425* (2013.01); *A61F 2/447* (2013.01); *A61F 2/4455* (2013.01)
(58) Field of Classification Search
CPC ..... A61F 2/4425; A61F 2/4455; A61F 2/446; A61F 2/4465; A61F 2/447
USPC ............................................ 623/17.11–17.16
See application file for complete search history.

(56) References Cited

U.S. PATENT DOCUMENTS

| | | |
|---|---|---|
| 5,904,719 A | 5/1999 | Errico et al. |
| 6,039,761 A | 3/2000 | Li et al. |
| 6,190,414 B1 | 2/2001 | Young et al. |
| 6,387,130 B1 | 5/2002 | Stone et al. |
| 6,706,070 B1 | 3/2004 | Wagner et al. |
| 6,712,819 B2 | 3/2004 | Zucherman et al. |
| 7,018,413 B2 | 3/2006 | Kruger |
| 7,641,690 B2 | 1/2010 | Abdou |
| 7,655,042 B2 * | 2/2010 | Foley et al. ................ 623/17.11 |
| 2002/0183754 A1 | 12/2002 | Michelson |
| 2005/0096745 A1 | 5/2005 | Andre et al. |
| 2005/0113920 A1 | 5/2005 | Foley et al. |
| 2005/0119747 A1 | 6/2005 | Fabris Monterumici et al. |
| 2006/0142858 A1 | 6/2006 | Colleran et al. |
| 2007/0067035 A1 | 3/2007 | Falahee |
| 2007/0260314 A1 | 11/2007 | Biyani |

* cited by examiner

*Primary Examiner* — Nicholas Woodall
(74) *Attorney, Agent, or Firm* — Suiter Swantz pc llo

(57) ABSTRACT

An interbody spacer implant for interbody fusion in a vertebral body comprises a spacer and an elongated insertion mechanism adapted to allow the spacer to articulate with respect to a pivot point.

16 Claims, 20 Drawing Sheets

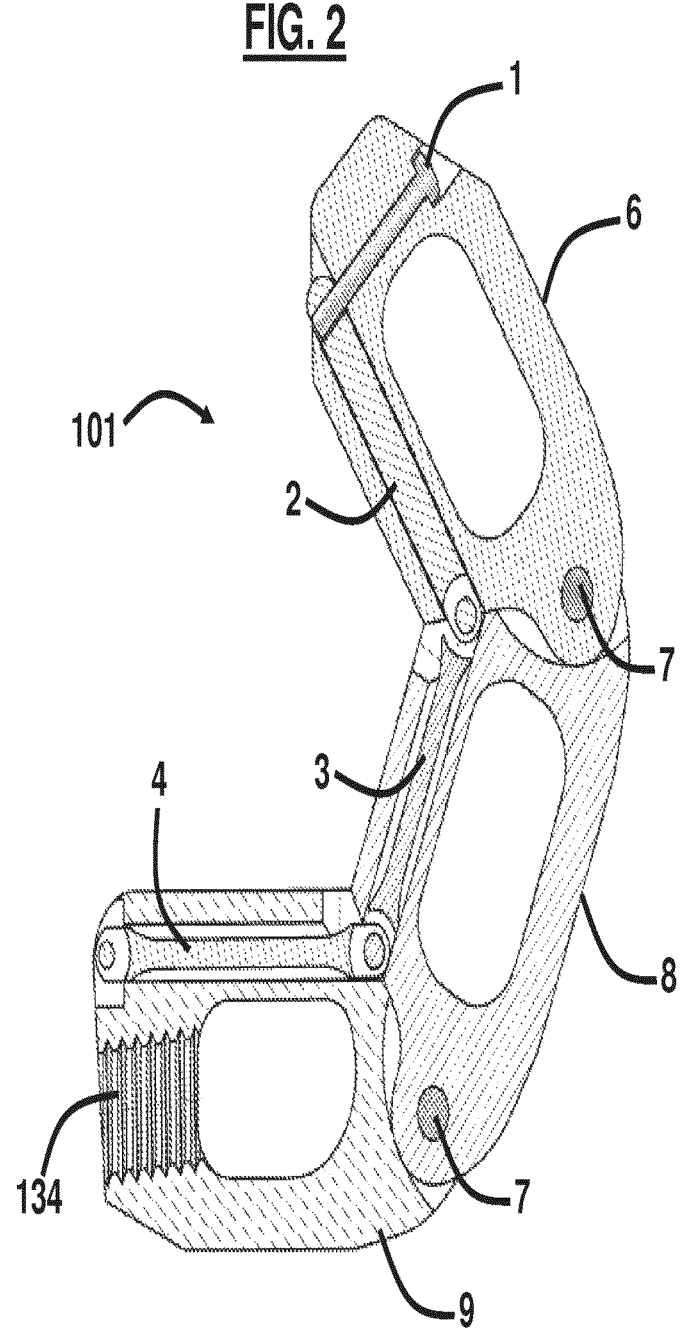

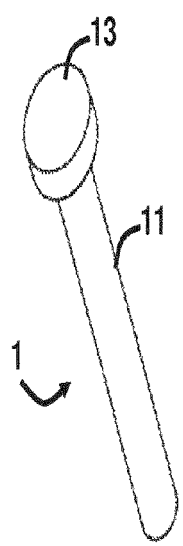
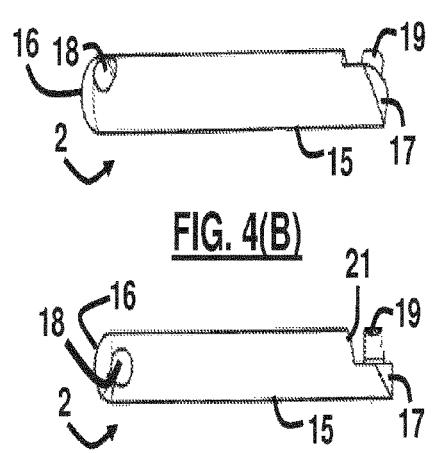
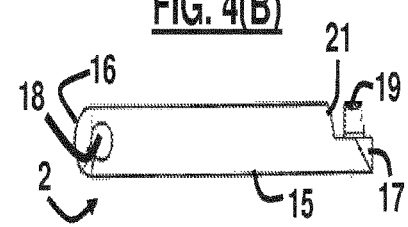
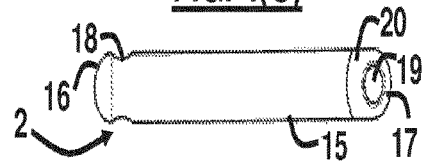

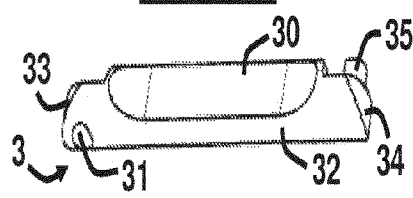
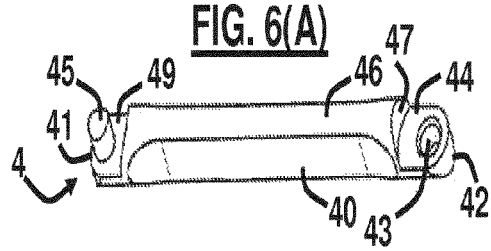
FIG. 5(A) FIG. 6(A)
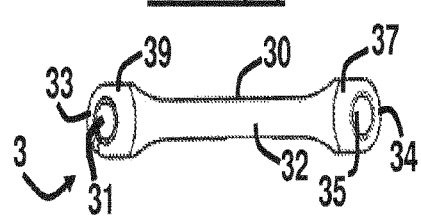
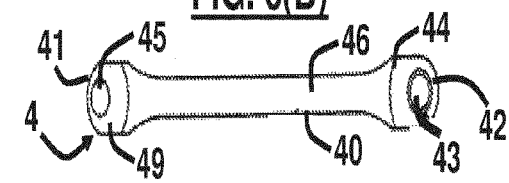
FIG. 5(B) FIG. 6(B)
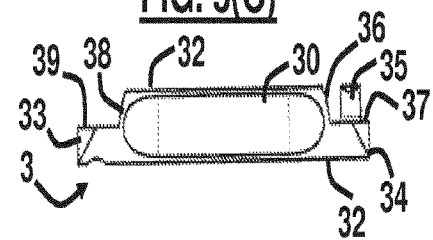
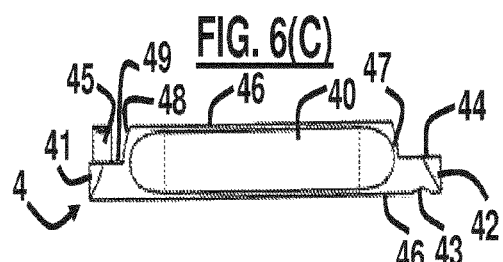
FIG. 5(C) FIG. 6(C)
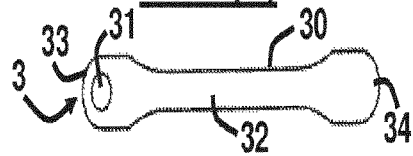
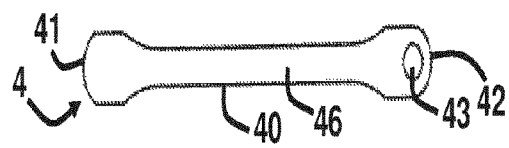
FIG. 5(D) FIG. 6(D)
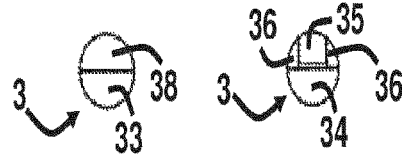
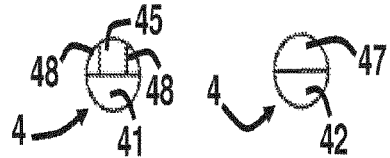
FIG. 5(E) FIG. 5(F) FIG. 6(E) FIG. 6(F)

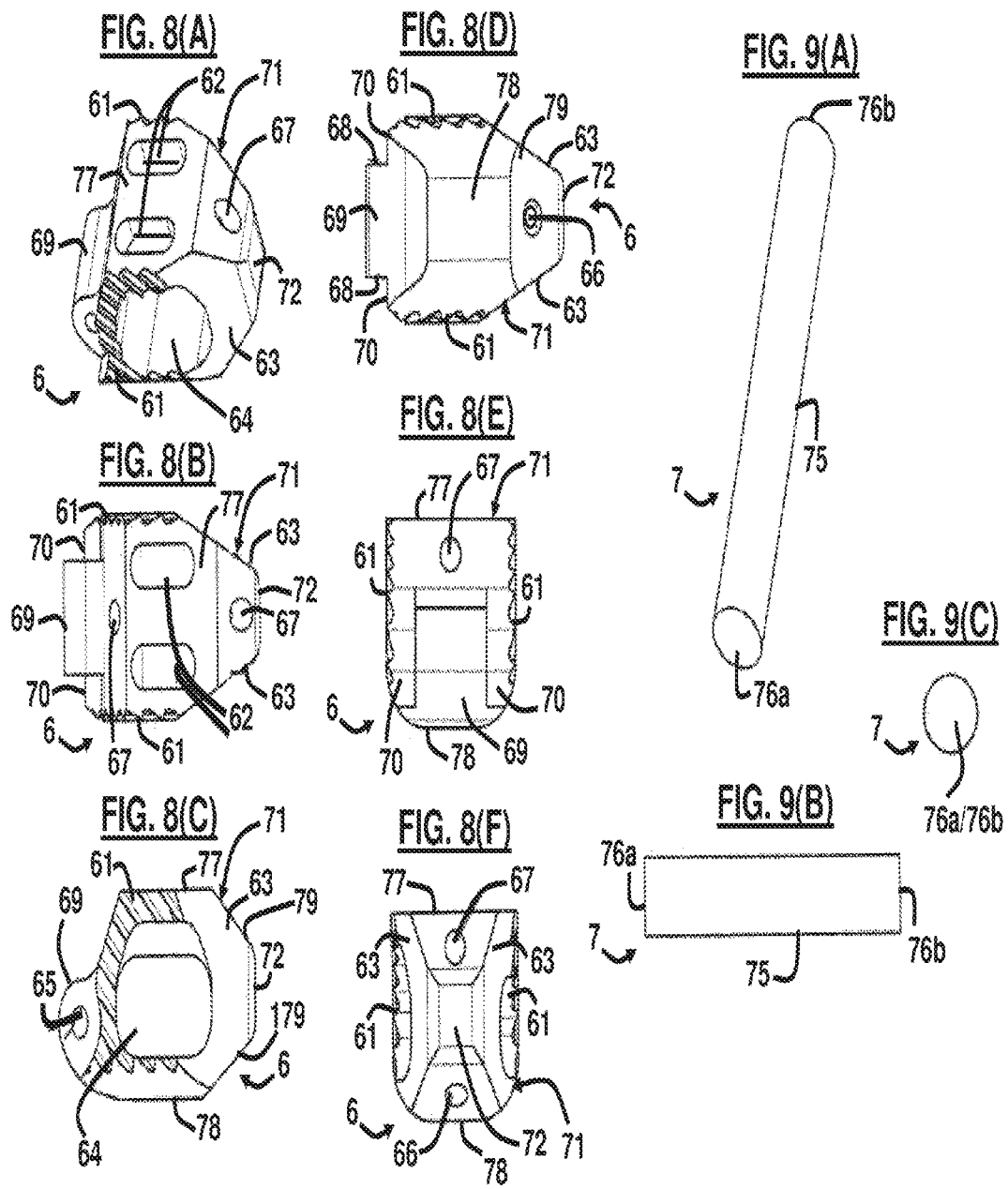

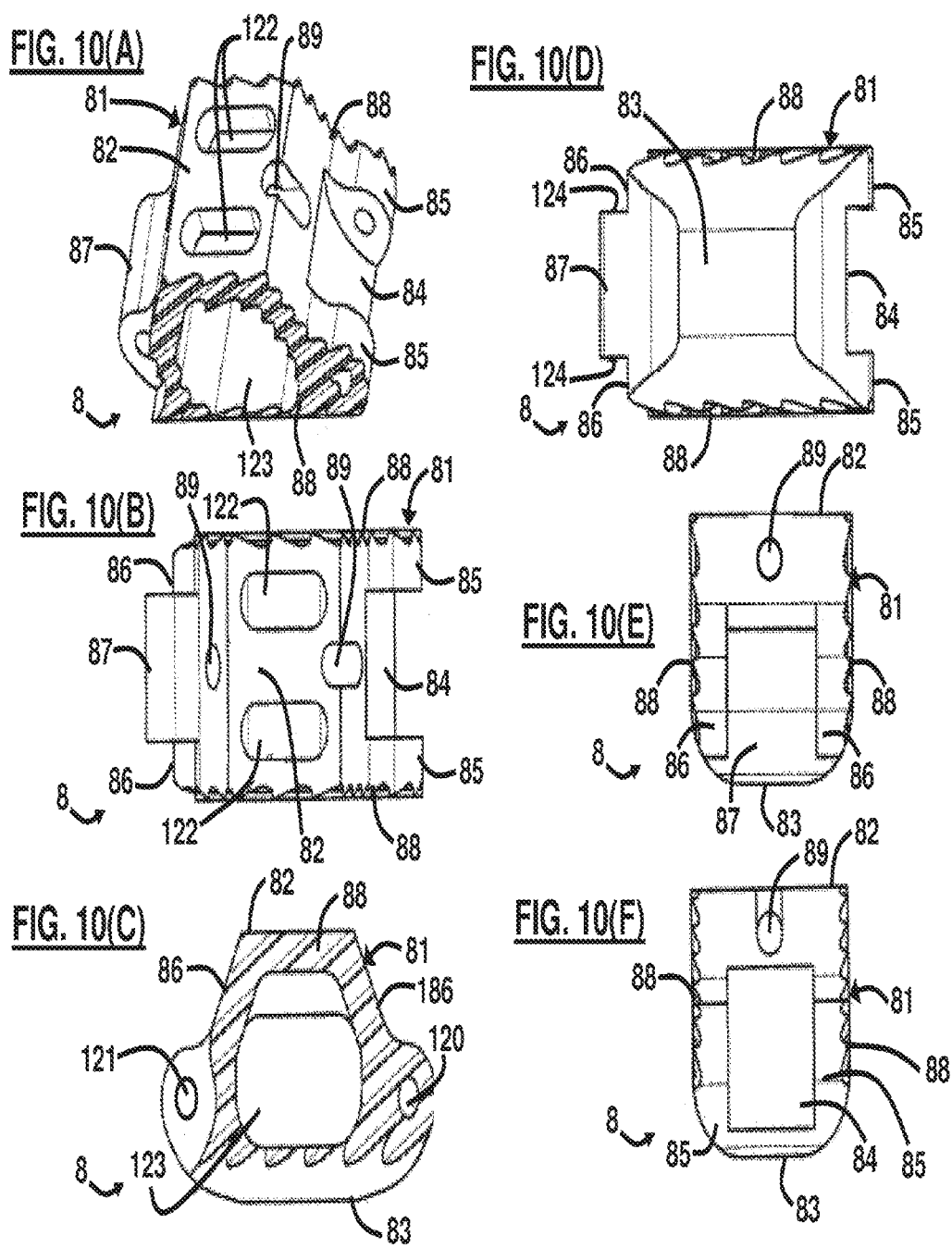

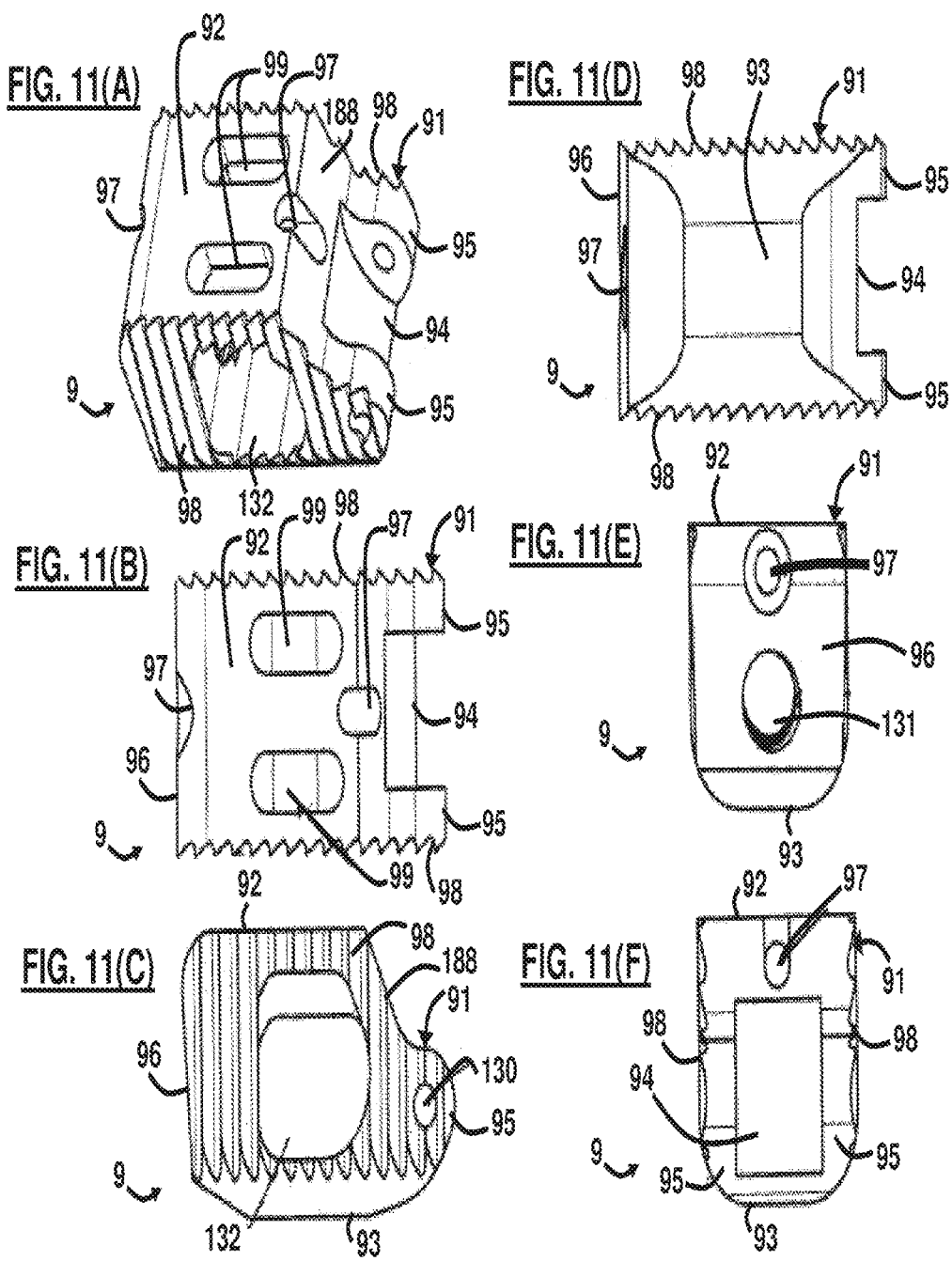

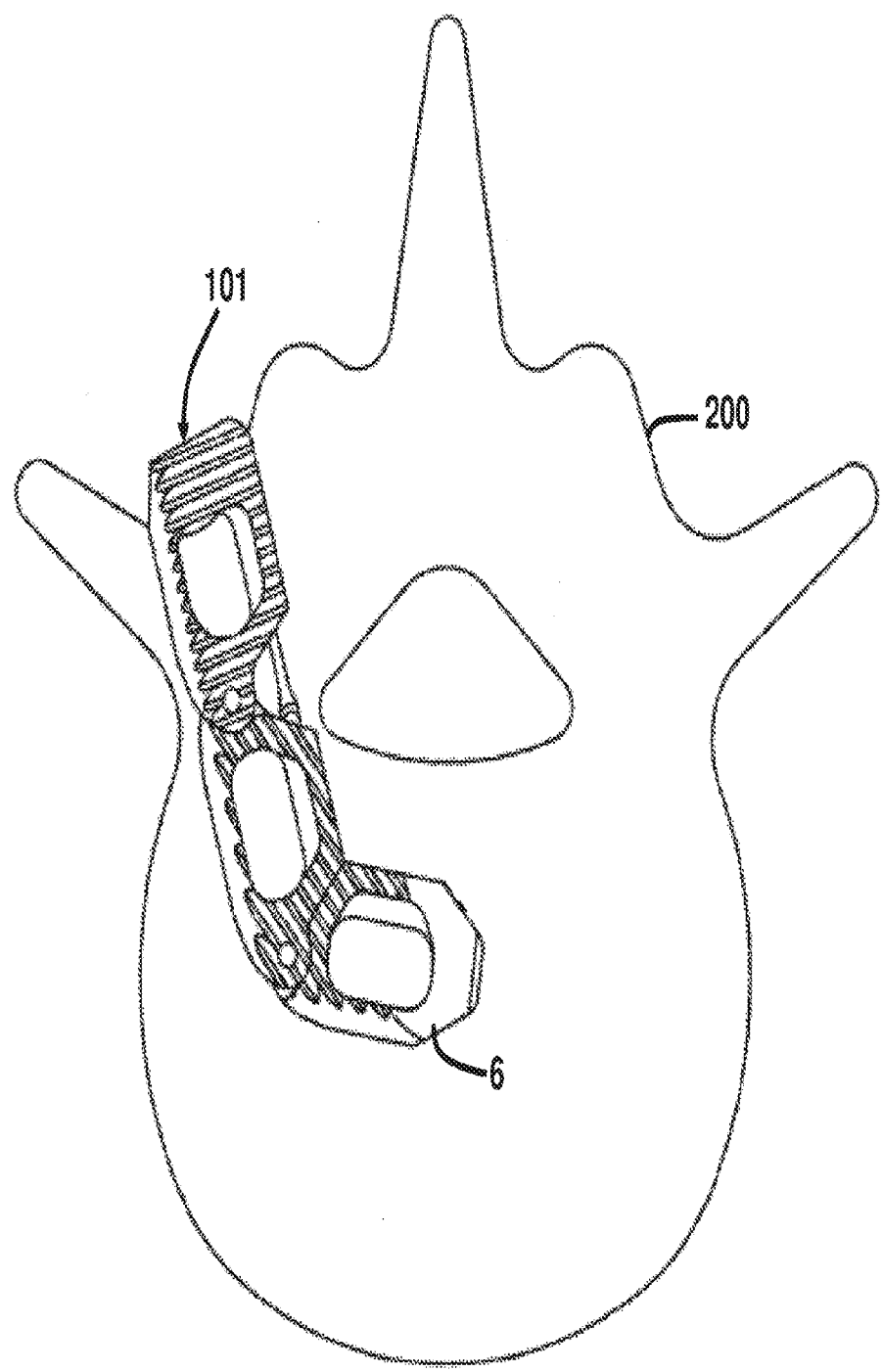

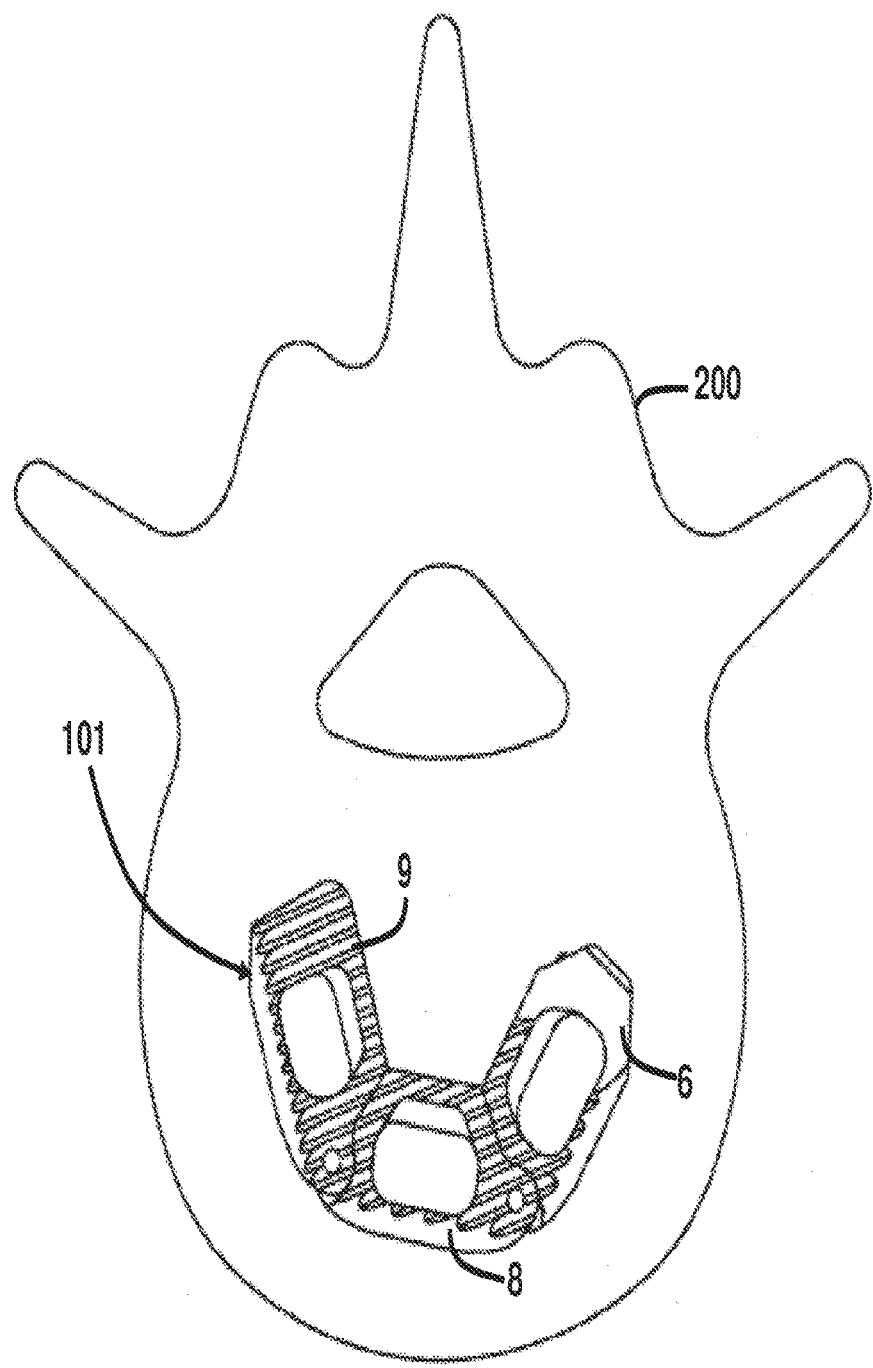

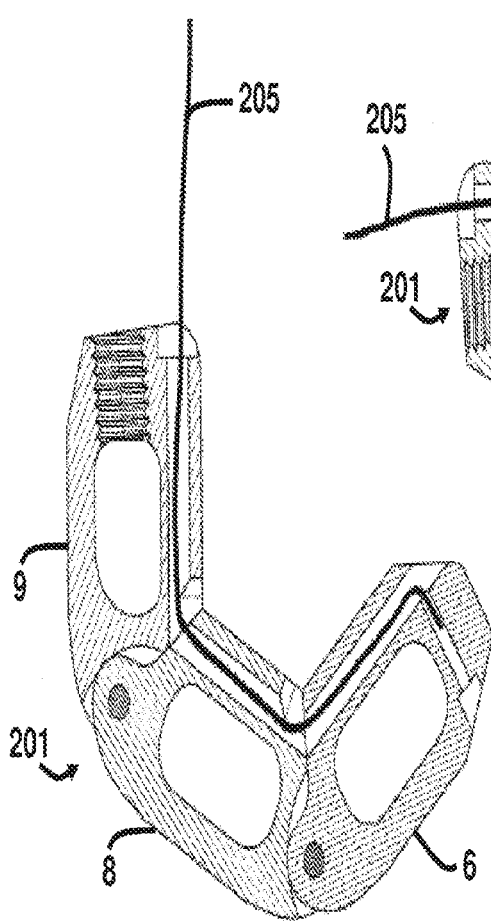
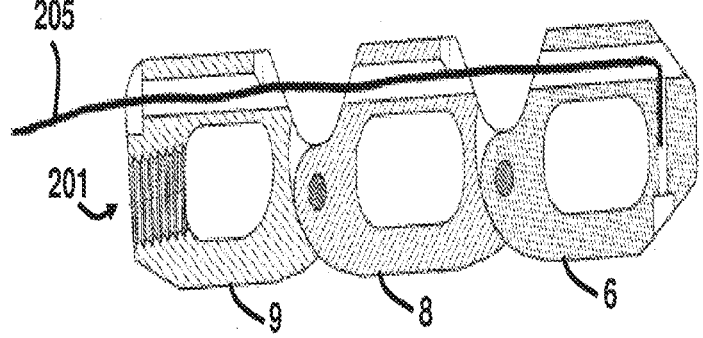
FIG. 15(A)
FIG. 15(B)

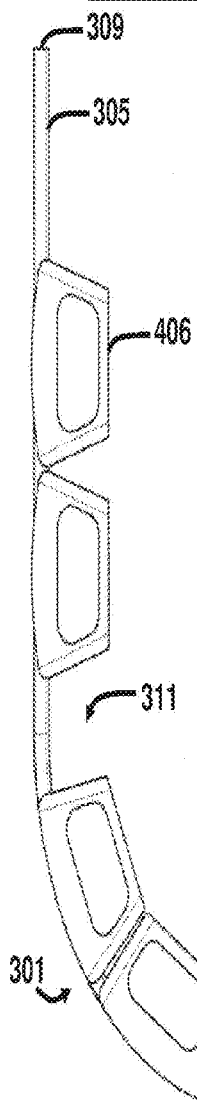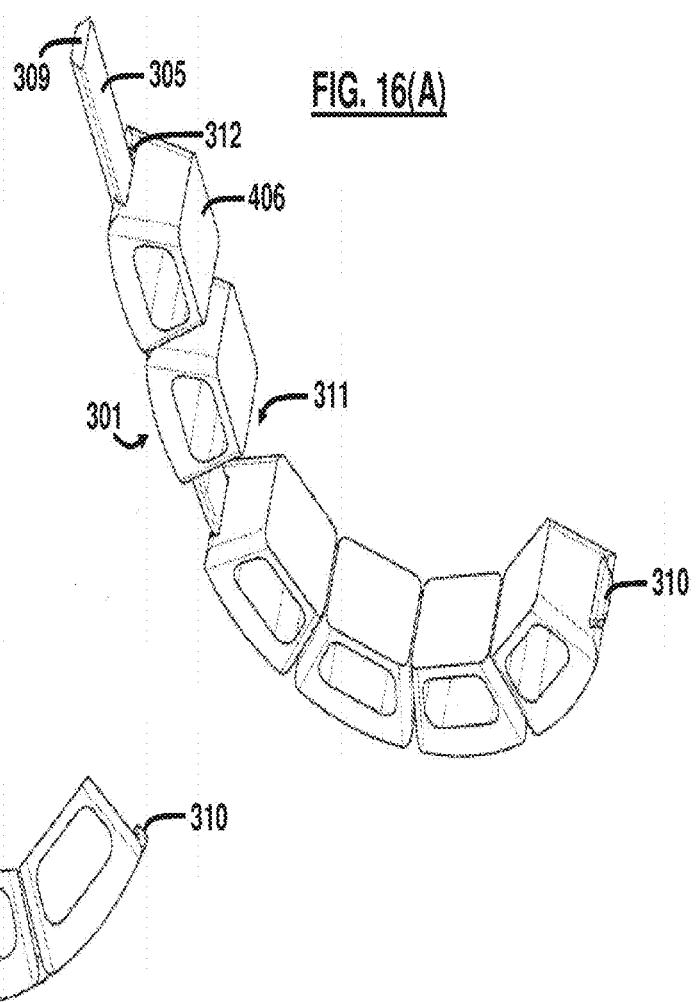

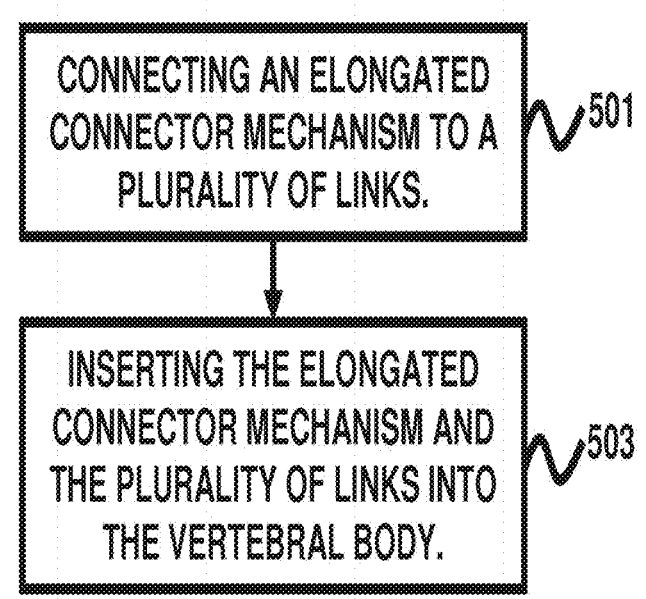

PIVOTING INTERBODY VERTEBRAL SPACER

CROSS-REFERENCE

This application is a continuation of U.S. patent application Ser. No. 13/189,939 (filed Jul. 25, 2011), which is a divisional of U.S. patent application Ser. No. 11/533,782 (filed Sep. 21, 2006), now patented as U.S. Pat. No. 8,025,697 (issued Sep. 27, 2011). U.S. patent application Ser. No. 11/533,782 (filed Sep. 21, 2006), and all continuing applications thereof are hereby incorporated by reference, in their entireties.

FIELD OF THE INVENTION

The embodiments herein generally relate to medical devices, and, more particularly, to implantable devices used to stabilize the human spine.

BACKGROUND OF THE INVENTION

The spinal column is a highly flexible structure comprising bones and connective tissue. While, the spine is capable of multiple degrees of motion, spinal injuries or anatomical irregularities may result in spinal pathologies which limit this range of motion. Orthopedic surgeons often aim to correct spinal irregularities and restore stability to traumatized through immobilization of spinal components.

Most conventional vertebral spacers and inter body devices do not provide adequate surface coverage and ease of ideal positioning, and others are generally too large or bulky to be inserted in the traditional posterior or transforaminal lumbar interbody approaches. The conventional large-sized spacers that may provide this adequate surface coverage typically must be inserted from an anterior or extreme lateral approach.

An example of a vertebral spacer is described in U.S. Pat. No. 7,018,413, the complete disclosure of which, in its entirety, is herein incorporated by reference. Generally, the conventional designs do not provide the surface coverage and ideal placement located towards the anterior side of the vertebral endplate while being implanted through a narrow passageway for transforaminal lumbar interbody fusion (TLIF) or posterior lumbar interbody fusion (PLIF) approaches. Generally, surgeons must lightly impact a spacer laterally towards the medial anterior side, and then try to position it medially once inside the spinal column to get more even coverage. Due to nerve anatomy, this can be a difficult task even for skilled surgeons.

Accordingly, there remains a need for a new spinal spacer capable of being properly inserted towards the anterior side of the vertebral endplate and which can be easily constructed and ultimately used by a surgeon during a spinal surgical procedure.

SUMMARY

In view of the foregoing, an embodiment provides an interbody spacer implant assembly for interbody fusion in a vertebral body, wherein the assembly comprises a plurality of links and an elongated connector mechanism adapted to retain the plurality of links and allow the plurality of links to articulate with respect to one another. Preferably, one of the plurality of links comprises a body portion comprises partially serrated sides; at least one first hole configured through a top of the body portion; a second hole configured through a side of the body portion and transverse to the at least first hole; a third hole configured through the body portion and transverse to the second hole; a fourth hole configured substantially parallel to the at least one first hole; a connector mechanism positioned transverse to the partially serrated sides; and a fifth hole configured through the connector mechanism.

Additionally, one of the plurality of links preferably comprises a body portion comprising serrated sides; at least one first hole configured through a top of the body portion; a second hole configured through a side of the body portion and transverse to the at least first hole; a third hole configured through the body portion and transverse to the second hole; a pair of connector flanges positioned transverse to the serrated sides; a fourth hole configured through each of the pair of connector flanges; a connector mechanism positioned transverse to the serrated sides; and a fifth hole configured through the connector mechanism.

Moreover, one of the plurality of links may comprise a body portion comprising serrated sides; at least one first hole configured through a top of the body portion; a second hole configured through a side of the body portion and transverse to the at least first hole; a third hole configured through the body portion and transverse to the second hole; a pair of connector flanges positioned transverse to the serrated sides; a fourth hole configured through each of the pair of connector flanges; and a fifth hole configured through a rear portion of the body portion.

The assembly may further comprise a hinge pin adapted to connect a first link of the plurality of links to a second link of the plurality of links. Furthermore, the elongated connector mechanism preferably comprises a plurality of pivoting connecting rods pivotally connected to one another. Moreover, one of the plurality of pivoting connecting rods may comprise a body portion; a peg; and a hole, wherein the peg and the hole are positioned on opposite sides of the body portion, wherein the body portion may comprise a pair of substantially flat side surfaces.

Additionally, the assembly may further comprise a retaining pin adapted to retain the elongated connector mechanism to one of the plurality of links. Preferably, a first link of the plurality of links is pivotally connected to a second link of the plurality of links. Also, the second link of the plurality of links is preferably pivotally connected to a third link of the plurality of links. Also, the elongated connector mechanism is preferably flexible. Furthermore, each one of the plurality of links may comprise a groove and a hole configured through a side of the each of the plurality of links. Moreover, the elongated connector mechanism may comprise a substantially J-shaped mechanism adapted to allow the plurality of links to slide thereon. Additionally, the plurality of links may comprise a continuous flexible structure. Preferably, the connector mechanism is dimensioned and configured to have a length-to-width ratio greater than a length-to-width ratio of each of the plurality of links.

Another embodiment provides an interbody spacer implant apparatus for interbody fusion in a vertebral body, wherein the apparatus comprises a plurality of individually articulating links and a connector mechanism adapted to retain the plurality of links and allow the plurality of links to articulate with respect to one another, wherein the connector mechanism is dimensioned and configured to have a length-to-width ratio greater than a length-to-width ratio of each of the plurality of links. The apparatus may further comprise an insertion rod adapted to insert the plurality of links and the connector mechanism into the vertebral body.

Another embodiment provides a method of inserting an interbody spacer implant assembly for interbody fusion into a vertebral body, wherein the method comprises connecting an elongated connector mechanism to a plurality of links; and inserting the elongated connector mechanism and the plurality of links into the vertebral body, wherein specified ones of individual links of the plurality of links are adapted to articulate individually with respect to other individual links upon insertion into the vertebral body. The method may further comprise attaching an insertion rod to the elongated connector mechanism; using the insertion rod to push the elongated connector mechanism and the plurality of links into the vertebral body; and removing the insertion rod from the elongated connector mechanism upon full insertion and final positioning of the elongated connector mechanism and the plurality of links into the vertebral body.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2 illustrates a schematic diagram of an articulating interbody spacer assembly according to an embodiment herein;

FIGS. 3(A) through 3(C) illustrate schematic diagrams of the retaining pin of the articulating interbody spacer apparatus of FIGS. 1(A) through 1(G) according to an embodiment herein;

FIGS. 4(A) through 4(F) illustrate schematic diagrams of the first hinged rod of the articulating interbody spacer apparatus of FIGS. 1(A) through 1(G) according to an embodiment herein;

FIGS. 5(A) through 5(F) illustrate schematic diagrams of the second hinged rod of the articulating interbody spacer apparatus of FIGS. 1(A) through 1(G) according to an embodiment herein;

FIGS. 6(A) through 6(F) illustrate schematic diagrams of the third hinged rod of the articulating interbody spacer apparatus of FIGS. 1(A) through 1(G) according to an embodiment herein;

FIGS. 8(A) through 8(F) illustrate schematic diagrams of the first link of the articulating interbody spacer apparatus of FIGS. 1(A) through 1(G) according to an embodiment herein;

FIGS. 9(A) through 9(C) illustrate schematic diagrams of the hinge pin of the articulating interbody spacer apparatus of FIGS. 1(A) through 1(G) according to an embodiment herein;

FIGS. 10(A) through 10(F) illustrate schematic diagrams of the second link of the articulating interbody spacer apparatus of FIGS. 1(A) through 1(G) according to an embodiment herein;

FIGS. 11(A) through 11(F) illustrate schematic diagrams of the third link of the articulating interbody spacer apparatus of FIGS. 1(A) through 1(G) according to an embodiment herein;

FIGS. 12(A) through 12(F) are schematic diagrams illustrating subsequent stages of insertion of the articulating interbody spacer assembly of FIG. 2 into a vertebral body according to an embodiment herein;

FIGS. 15(A) and 15(B) are schematic diagrams of a third alternate embodiment of an articulating interbody spacer assembly according to the embodiments herein;

FIGS. 16(A) and 16(B) are schematic diagrams of a fourth alternate embodiment of an articulating interbody spacer assembly according to the embodiments herein; and FIG. 17 is a flow diagram illustrating a preferred method according to an embodiment herein.

DETAILED DESCRIPTION OF PREFERRED EMBODIMENTS

Figure 1A:
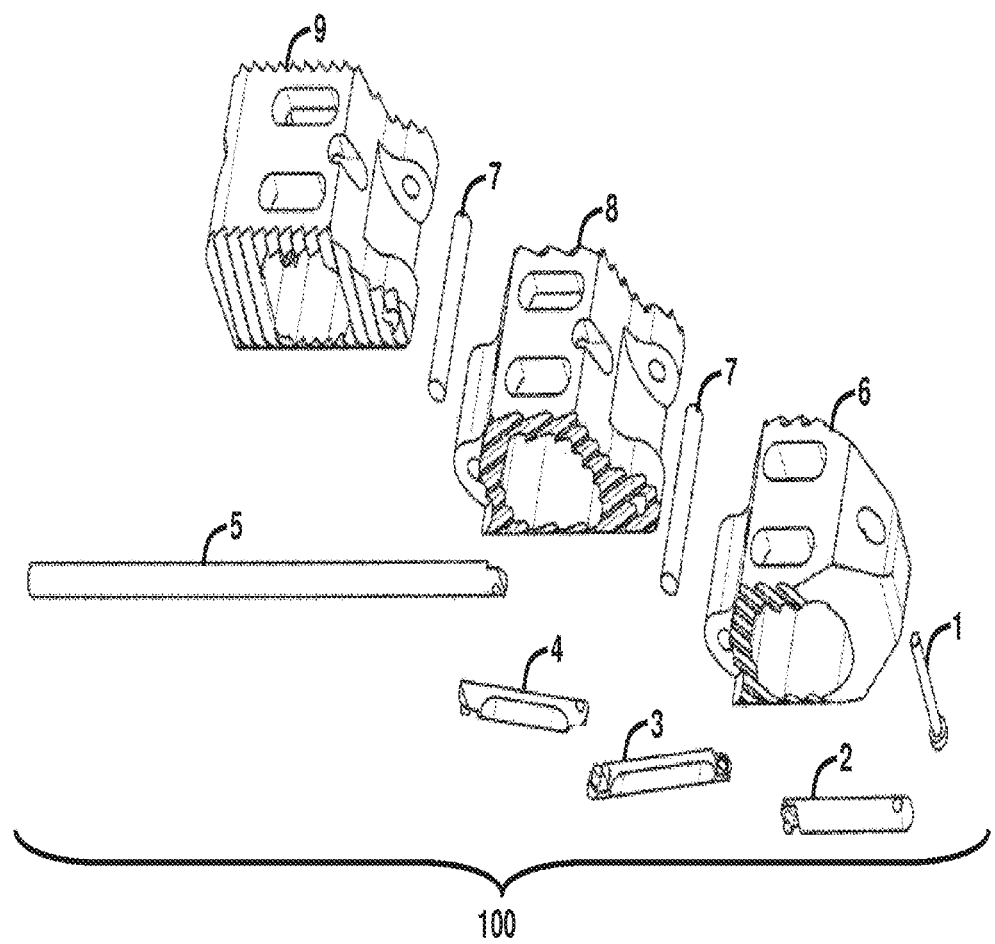
FIG. 1(A) illustrates an exploded schematic diagram of an articulating interbody spacer apparatus according to an embodiment herein.
Figure 1B:
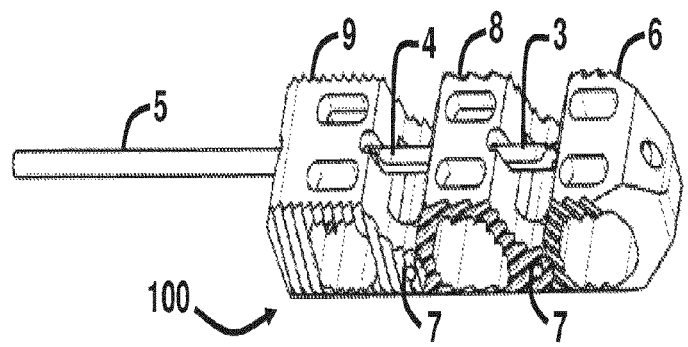
FIGS. 1(B) through 1(G) illustrate schematic diagrams of the articulating interbody spacer apparatus of FIG. 1(A) according to an embodiment herein.
Figure 1C:
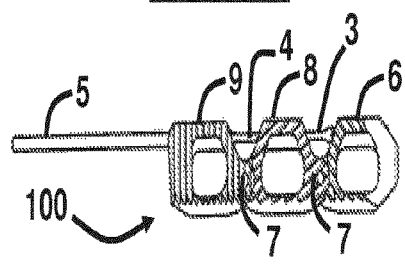
Figure 1D:
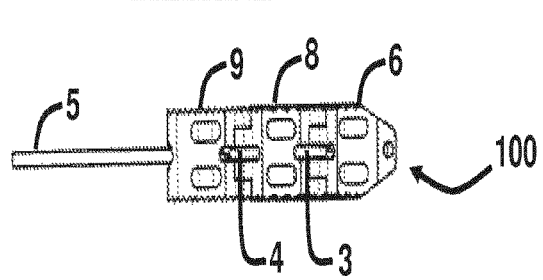
Figure 1E:
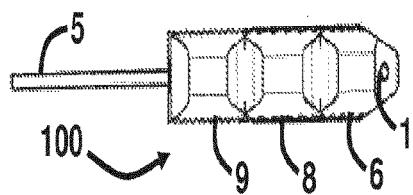
Figure 1F:
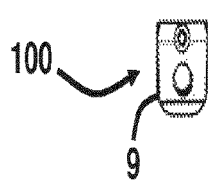
Figure 1G:
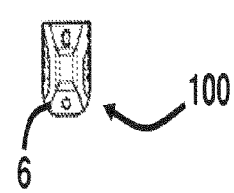
Figure 7A:
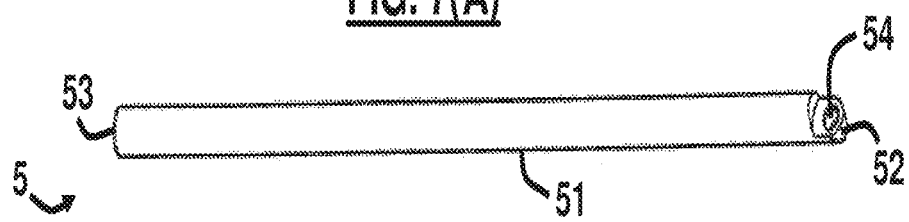
FIGS. 7(A) through 7(F) illustrate schematic diagrams of the insertion rod of the articulating interbody spacer apparatus of FIGS. 1(A) through 1(G) according to an embodiment herein.
Figure 7B:
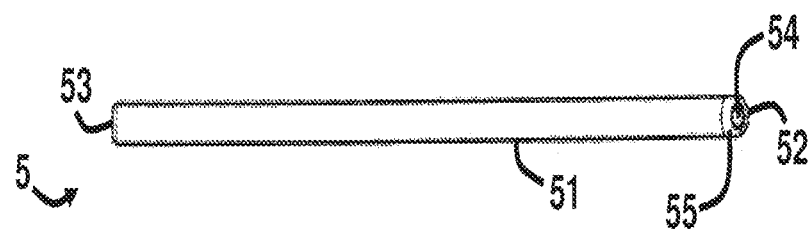
Figure 7C:
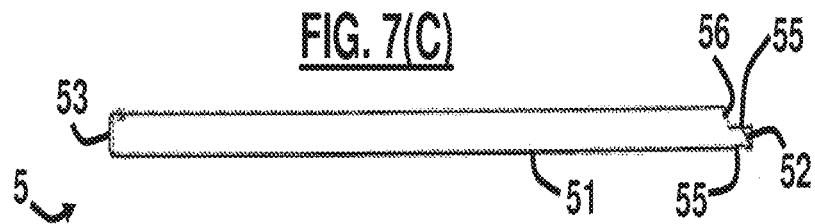
Figure 7D:
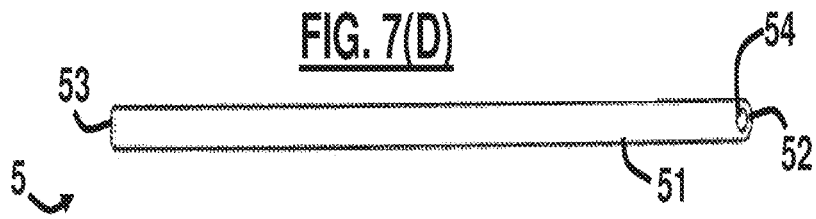
Figure 7E:
Figure 7F:
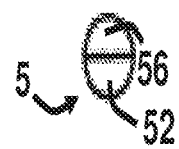
Figure 12A:
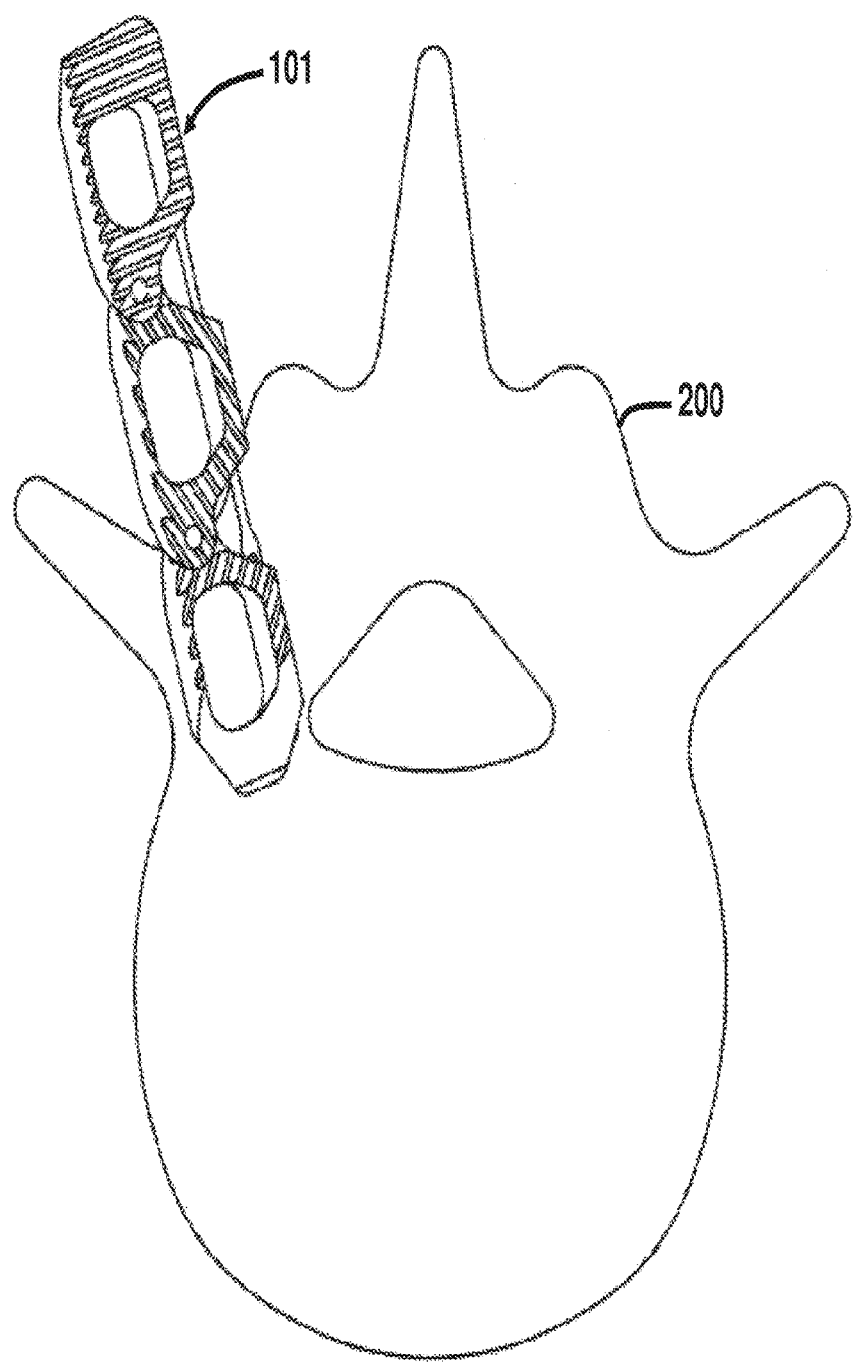
Figure 12B:
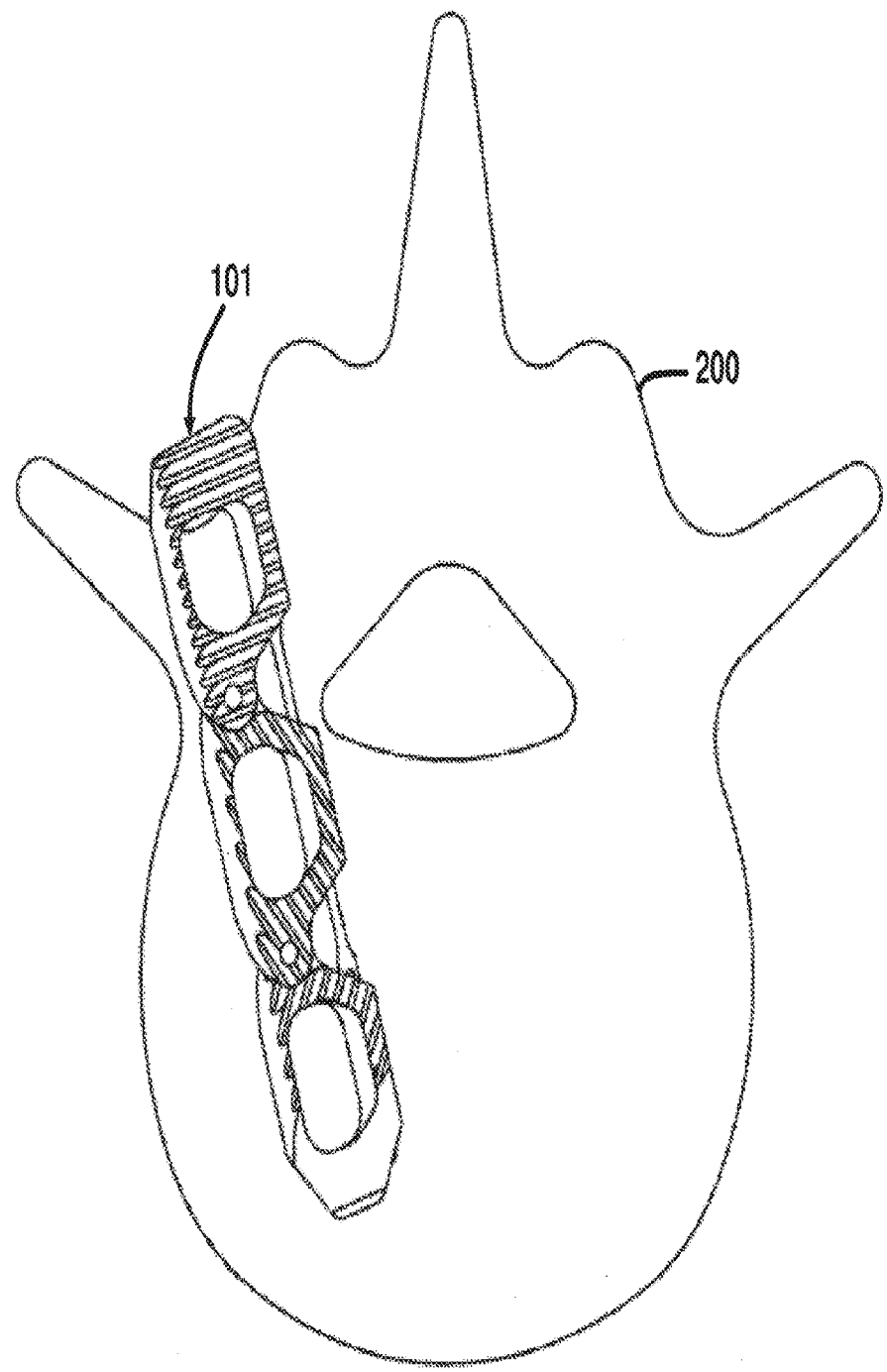
Figure 12D:
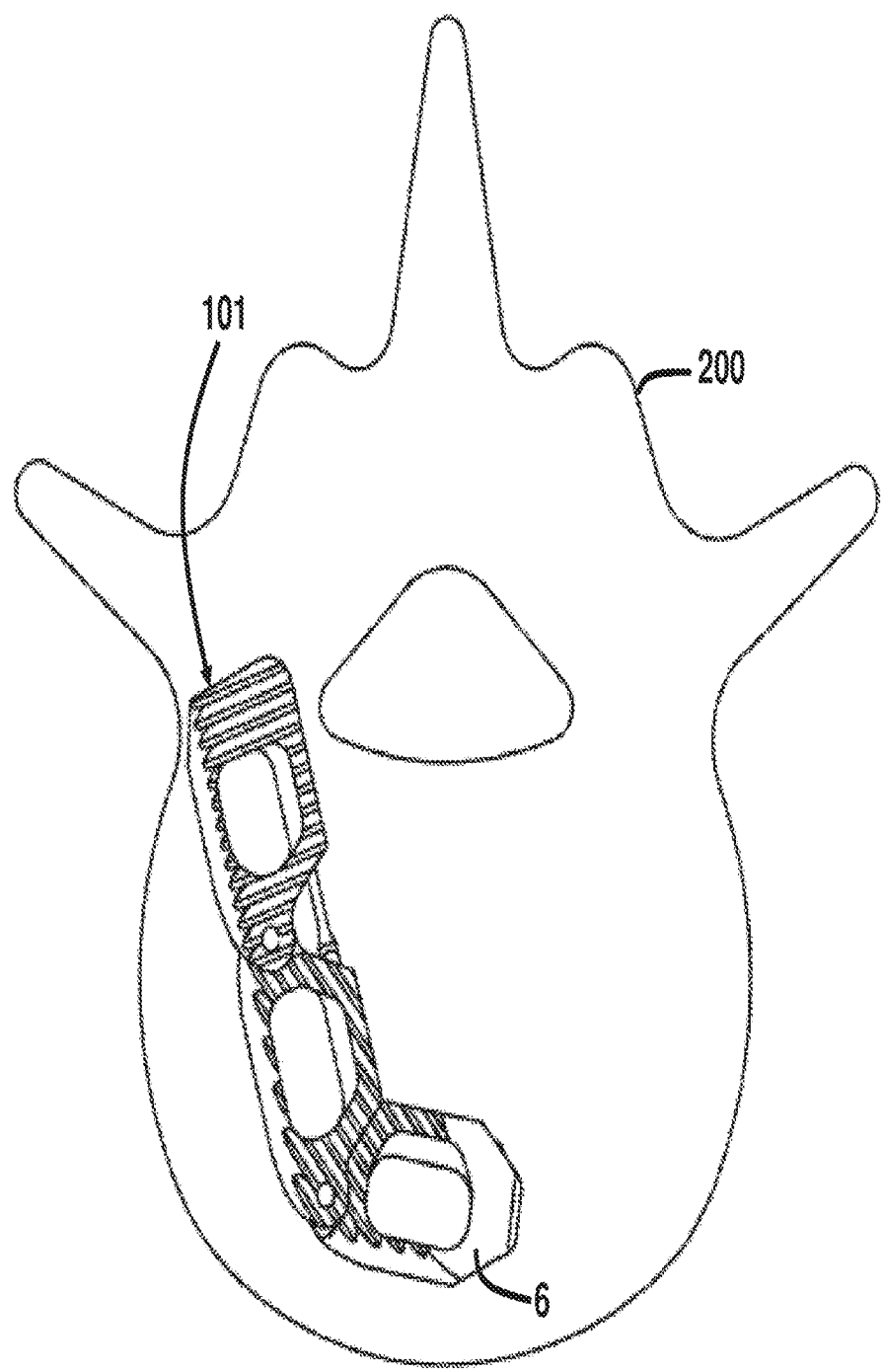
Figure 12E:
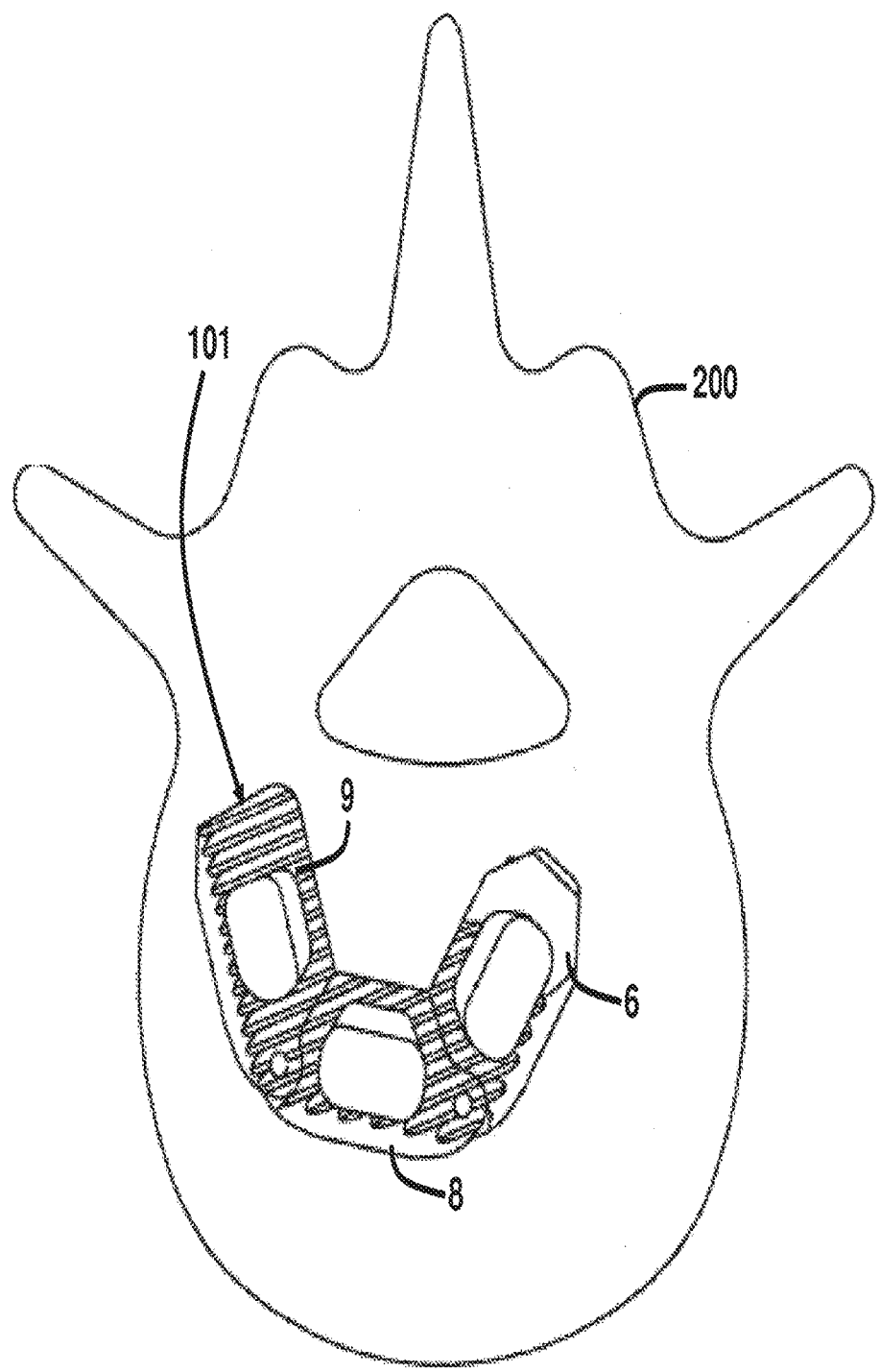

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new spinal spacer capable of being properly inserted towards the anterior side of the vertebral endplate and which can be easily constructed and ultimately used by a surgeon during a spinal surgical procedure. The embodiments herein achieve this by providing an articulating interbody spacer that is dimensioned and configured to be inserted through a proportionately narrow passageway and which provides optimal surface coverage and placement, thereby reducing the chances of subsidence into the vertebral endplates. Referring now to the drawings, and more particularly to FIGS. 1(A) through 17, where similar reference characters denote corresponding features consistently throughout the figures, there are shown preferred embodiments.

FIGS. 1(A) through 1(G) illustrate various views of an articulating interbody spacer apparatus 100 according to an embodiment herein. Generally, the apparatus 100 comprises a retaining pin 1, a first hinged rod 2, a second hinged rod 3, a third hinged rod 4, an insertion rod 5, a first link 6, a second link 8, third link 9, and a plurality of hinge pins 7. One of the hinge pins 7 is used to connect the first link 6 to the second link 8, while the other hinge pin 7 is used to connect the second link 8 to the third link 9. Moreover, the first hinged rod 2 is adapted to connect to the second hinged rod 3, and the second hinged rod 3 is adapted to connect to the third hinged rod 4. The retaining pin 1 is adapted to securely connect the first hinged rod 2 to the first link 6, and the insertion rod 5 is adapted to connect to the third hinged rod 4, whereby the insertion rod 5 is adapted to be disconnected from the third hinged rod 4.

FIG. 2 illustrates a schematic diagram of an articulating interbody spacer assembly 101 according to an embodiment herein. The difference between the assembly 101 of FIG. 2 and the apparatus of FIGS. 1(A) through 1(G) is that the assembly 101 does not include the insertion rod 5 (i.e., after the insertion rod 5 has been disconnected from the third hinged rod 4). As FIG. 2 illustrates, the first link 6, second link 8, and third link 9 are pivotally connected to one another in the manner described above by using the hinge pins 7 for the various connections (i.e., connection of the first link 6 to the second link 8 and the connection of the second link 8 to the third link 9), and as such allows the assembly 101 to articulate from a generally straight position to a generally curved position.

FIGS. 3(A) through 3(C) illustrate schematic diagrams of the retaining pin 1 of the articulating interbody spacer apparatus 100 of FIGS. 1(A) through 1(G) according to an embodiment herein. The retaining pin 1 comprises a shaft 11 with a cap portion 13 positioned on top of the shaft 11. Moreover, the cap portion 13 has an exposed under surface 12 such that the circumferential configuration of the cap portion 13 is preferably larger than the circumferential configuration of the shaft 11.

FIGS. 4(A) through 4(F) illustrate schematic diagrams of the first hinged rod 2 of the articulating interbody spacer apparatus 100 of FIGS. 1(A) through 1(G) according to an embodiment herein. The first hinged rod 2 is generally embodied in an elongated configuration. The first hinged rod 2 comprises an elongated body portion 15 that is generally rounded terminating in a pair of ends 16, 17 opposed from one another. The first end 17 of the body portion 15 is defined by an upper generally flat base 20 bounded by a generally sloping wall 21. A pivot peg 19 outwardly extends from the flat base 20 in a generally perpendicular manner. The upper surface of the flat base 20 is positioned below the upper surface of the body portion 15 such that the upper surface of the pivot peg 19 may be substantially planar to the upper surface of the body portion 15. The second end 16 of the body portion 15 comprises a retention hole 18 configured substantially transverse to the longitudinal axis of the body portion 15.

FIGS. 5(A) through 5(F) illustrate schematic diagrams of the second hinged rod 3 of the articulating interbody spacer apparatus 100 of FIGS. 1(A) through 1(G) according to an embodiment herein. The second hinged rod 3 is generally embodied in an elongated configuration and comprises two generally rounded longitudinal sides 32 and two substantially flat sides 30. The flat sides 30 allow for flexion in the needed direction during articulation of the second hinged rod 3. A pair of ends 33, 34 opposed from one another is also provided on the second hinged rod 3. The first end 34 is defined by an upper generally flat base 37 bounded by a generally sloping wall 36. A pivot peg 35 outwardly extends from the flat base 37 in a generally perpendicular manner. The upper surface of the flat base 37 is positioned below the upper surface of the top generally rounded longitudinal side 32 such that the upper surface of the pivot peg 35 may be substantially planar to the upper surface of the top generally rounded longitudinal side 32. The second end 33 comprises a generally flat upper surface 39 bounded by a generally sloping wall 38. The second end 33 further includes a pivot hole 31 configured substantially transverse to the longitudinal axis of the two generally rounded longitudinal sides 32 and two substantially flat sides 30.

FIGS. 6(A) through 6(F) illustrate schematic diagrams of the third hinged rod 4 of the articulating interbody spacer apparatus 100 of FIGS. 1(A) through 1(G) according to an embodiment herein. The third hinged rod 4 is generally embodied in an opposite configuration of the second hinged rod 3. The third hinged rod 4 also comprises a generally elongated configuration and includes two generally rounded longitudinal sides 46 and two substantially flat sides 40. The flat sides 40 allow for flexion in the needed direction during articulation of the third hinged rod 4. A pair of ends 41, 42 opposed from one another is also provided on the third hinged rod 4. The first end 42 comprises a generally flat upper surface 44 bounded by a generally sloping wall 47. The first end 42 further includes a pivot hole 43 configured substantially transverse to the longitudinal axis of the two generally rounded longitudinal sides 46 and two substantially flat sides 40. The second end 41 is defined by an upper generally flat base 49 bounded by a generally sloping wall 48. A pivot peg 45 outwardly extends from the flat base 49 in a generally perpendicular manner. The upper surface of the flat base 49 is positioned below the upper surface of the top generally rounded longitudinal side 46 such that the upper surface of the pivot peg 45 may be substantially planar to the upper surface of the top generally rounded longitudinal side 46.

FIGS. 7(A) through 7(F) illustrate schematic diagrams of the insertion rod 5 of the articulating interbody spacer apparatus 100 of FIGS. 1(A) through 1(G) according to an embodiment herein. The insertion rod 5 is generally embodied in an elongated configuration. The insertion rod 5 comprises an elongated body portion 51 that is generally rounded terminating in a pair of ends 52, 53 opposed from one another. The first end 52 of the body portion 51 is defined by an upper generally flat base 55 bounded by a generally sloping wall 56. The upper surface of the flat base 55 is positioned below the upper surface of the body portion 51. The first end 52 further comprises a pivot hole 54 configured substantially transverse to the longitudinal axis of the body portion 51. The second end 53 is adapted to be attached to an inserter tool/mechanism (not shown).

FIGS. 8(A) through 8(F) illustrate schematic diagrams of the first link 6 of the articulating interbody spacer apparatus 100 of FIGS. 1(A) through 1(G) according to an embodiment herein. The first link 6 comprises a body portion 71 having a top end 77 and a bottom end 78, whereby the top end 77 is configured with a pair of vertical bone graft windows 62 that are adapted to allow for bone growth during fusion. The body portion 71 of the first link 6 also comprises a pair of opposed partially serrated sides 61 each terminating with unserrated tapered walls 63 towards a front end 72 of the body portion 71. The top end 77 terminates with a downwardly sloping wall 79 towards the front end 72. Moreover, the bottom end 78 terminates with an upwardly sloping wall 179 towards the front end 72. The back end of the body portion 71 comprises a generally sloping wall 70 having a connector mechanism 69 extending therefrom. The connector mechanism 69 has generally flat side surfaces 68 and a throughhole 65 configured transversely with respect to the longitudinal axis of the body portion 71. A rod retention hole 67 extends from the sloping wall 70 at the rear of the body portion 71 through to the sloping wall 79 at the front of the body portion 71. Additionally, the rod retention hole 67 extends through the upper part of the body portion 71 along a substantially longitudinal axis of the body portion 71 and is dimensioned and configured to accommodate the first hinged rod 2 of the apparatus 100 of FIGS. 1(A) through 1(G). Also, configured in the upwardly sloping wall 179 is a retention pin hole 66, which is dimensioned and configured to accommodate the retaining pin 1 of the apparatus 100 of FIGS. 1(A) through 1(G). A horizontal bone graft window 64 is positioned in the generally central part of the body portion 71 and is configured to be substantially transverse to the longitudinal axis of the body portion 71. In other words, the horizontal bone graft window 64 and the throughhole 65 are substantially parallel to one another.

FIGS. 9(A) through 9(C) illustrate schematic diagrams of the hinge pin 7 of the articulating interbody spacer apparatus 100 of FIGS. 1(A) through 1(G) according to an embodiment herein. The hinge pin 7 is generally configured in a cylindrical embodiment, although other configurations may be used in accordance with the embodiments herein. The hinge pin 7 comprises a shaft 75 terminating in a pair of ends 76a, 76b.

FIGS. 10(A) through 10(F) illustrate schematic diagrams of the second link 8 of the articulating interbody spacer apparatus 100 of FIGS. 1(A) through 1(G) according to an embodiment herein. The second link 8 comprises a body portion 81 having a top end 82 and a bottom end 83, whereby the top end 82 is configured with a pair of vertical bone graft windows 122 that are adapted to allow for bone growth during fusion. The body portion 81 of the second link 8 also comprises a pair of opposed serrated sides 88. The top end 82 terminates with a downwardly sloping wall 186, which then terminates with a further downwardly sloping wall 84 sandwiched in between a pair of connector flanges 85. Each connector flange 85 comprises a throughhole 120 aligned with one another. The rear of the body portion 81 comprises a generally sloping wall 86 having a connector mechanism 87 extending therefrom. The connector mechanism 87 has generally flat side surfaces 124 and a throughhole 121 configured transversely with respect to the longitudinal axis of the body portion 81. A rod retention hole 89 extends from the sloping wall 86 at the rear of the body portion 81 through to the sloping wall 186 at the front of the body portion 81. Additionally, the rod retention hole 89 extends through the upper part of the body portion 81 along a substantially longitudinal axis of the body portion 81 and is dimensioned and configured to accommodate portions of the second hinged rod 3 and third hinged rod 4 of the apparatus 100 of FIGS. 1(A) through 1(G). A horizontal bone graft window 123 is positioned in the generally central part of the body portion 81 and is configured to be substantially transverse to the longitudinal axis of the body portion 81. In other words, the horizontal bone graft window 123 and the throughhole 121 are substantially parallel to one another.

FIGS. 11(A) through 11(F) illustrate schematic diagrams of the third link 9 of the articulating interbody spacer apparatus 100 of FIGS. 1(A) through 1(G) according to an embodiment herein. The third link 9 comprises a body portion 91 having a top end 92 and a bottom end 93, whereby the top end 92 is configured with a pair of vertical bone graft windows 99 that are adapted to allow for bone growth during fusion. The body portion 91 of the third link 9 also comprises a pair of opposed serrated sides 98. The top end 92 terminates with a downwardly sloping wall 188, which then terminates with a further downwardly sloping wall 94 sandwiched in between a pair of connector flanges 95. Each connector flange 95 comprises a throughhole 130 aligned with one another. A rod retention hole 97 extends from the rear wall 96 of the body portion 91 through to the sloping wall 188 at the front of the body portion 91. Additionally, the rod retention hole 97 extends through the upper part of the body portion 91 along a substantially longitudinal axis of the body portion 91 and is dimensioned and configured to accommodate portions of the second hinged rod 3, the third hinged rod 4, and the insertion rod 5 of the apparatus 100 of FIGS. 1(A) through 1(G). A horizontal bone graft window 132 is positioned in the generally central part of the body portion 91 and is configured to be substantially transverse to the longitudinal axis of the body portion 91. Accordingly, the horizontal bone graft window 132 and the throughhole 130 are substantially parallel to one another. A threaded hole 131 extends through the lower part of the body portion 91 along a substantially longitudinal axis of the body portion 91 and has its opening at the rear wall 96. Preferably, threaded hole 131 is positioned off axis directed towards the top end 92 to keep the implant assembly 101 from articulating prematurely during impaction. Furthermore, rear wall 96 is preferably perpendicular to threaded hole 131 for the same reason.

FIGS. 12(A) through 12(F) are schematic diagrams illustrating subsequent stages of insertion of the articulating interbody spacer assembly 101 of FIG. 2 into a vertebral body 200 according to an embodiment herein. In practice, the assembly 101 will be inserted using the insertion rod 5. In the first stage of insertion shown in FIG. 12(A), the assembly 101 is in a generally straight configuration and is inserted into a previously drilled opening in the vertebral body 200. In the second stage of insertion shown in FIG. 12(B), the assembly 101 is still in a generally straight configuration and is nearly entirely inside the vertebral body 200. In the third stage of insertion shown in FIG. 12(C), the assembly 101 begins to articulate such that the first link 6 begins to pivot. In the fourth stage of insertion shown in FIG. 12(D), the assembly 101 is entirely within the vertebral body 200 with the first link 6 in its pivoted position. In the fifth stage of insertion shown in FIG. 12(E), the assembly 101 is entirely within the vertebral body 200 with each of the first, second, and third links 6, 8, 9 being in their respective pivoted positions. In the sixth stage of insertion shown in FIG. 12(F), the assembly 101 is in its final position of insertion (i.e., resting position) with each of the first, second, and third links 6, 8, 9 being in their respective pivoted positions.

Figure 13:
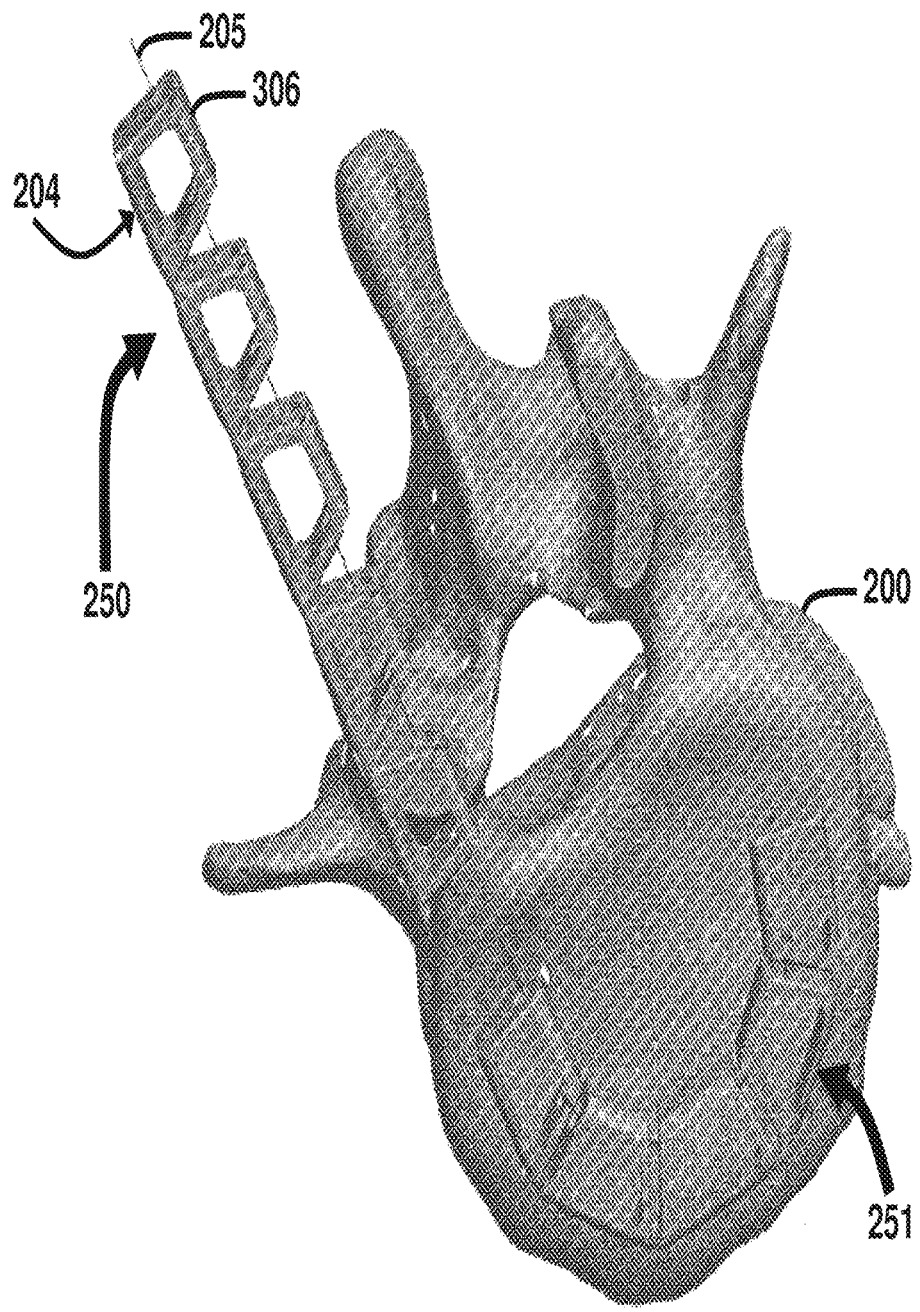
FIG. 13 is a schematic diagram of a first alternate embodiment of an articulating interbody spacer assembly according to the embodiments herein.

FIG. 13 is a schematic diagram of a first alternate embodiment of an articulating interbody spacer assembly 204 according to the embodiments herein. FIG. 13 illustrates the assembly in its initial position 250 as well as its articulated final position 251 within a vertebral body 200. In this embodiment (also referred to as a living hinge embodiment) the hinged links 306 of the implant are made of a single piece flexible material held together by a cable or guide wire 205 as opposed to having separate links 6, 8, 9 pivoting off a hinge pin 7.

Figure 14A:
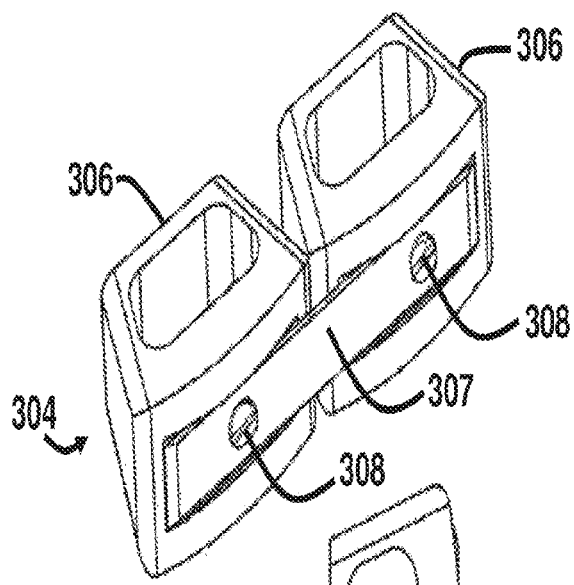
FIGS. 14(A) through 14(C) are schematic diagrams of a second alternate embodiment of an articulating interbody spacer assembly according to the embodiments herein.
Figure 14B:
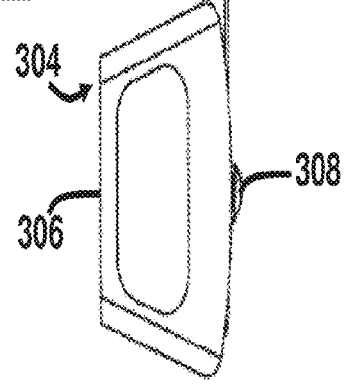
Figure 14C:
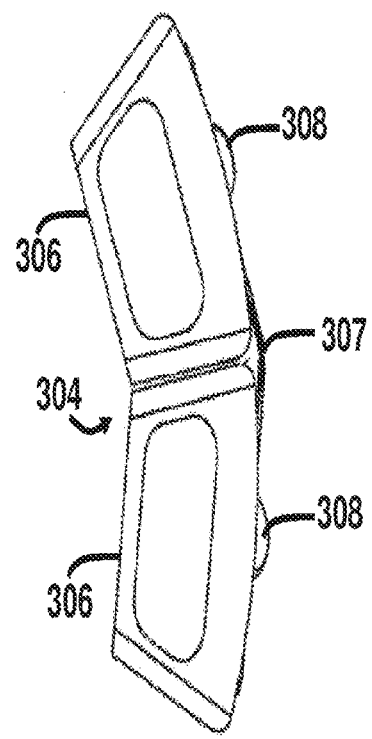

FIGS. 14(A) through 14(C) are schematic diagrams of a second alternate embodiment of an articulating interbody spacer assembly 304 according to the embodiments herein. This assembly 304 comprises links 306 connected by a flexible (living) hinge 307. Connection rivets 308 are used to attach the flexible hinge 307 to the links 306. The flexible hinge 307 is made of a separate material (with respect to the links 306) and is securely attached to the links 306 with proper spacing so that the links 306 can articulate to provide the desired articulating result. The flexible hinge 307 may comprise implantable stainless steel, titanium alloy, or nitinol. Moreover, the links 306 may comprise carbon fiber, PEEK optima, or titanium.

FIGS. 15(A) and 15(B) are schematic diagrams of a third alternate embodiment of an articulating interbody spacer assembly 201 according to the embodiments herein. This assembly 201 is similar to the assembly 101 of FIG. 2 except the first, second, and third hinged rods 2, 3, 4 of assembly 101 are replaced with a single cable or guide wire 205 that is allowed to flex or bend where the first, second, and third hinged links 6, 8, 9 respectively articulate.

FIGS. 16(A) and 16(B) are schematic diagrams of a fourth alternate embodiment of an articulating interbody spacer assembly 301 according to the embodiments herein. The assembly 301 comprises an implantable ramp 305 comprising an initially open end 309 and terminating with a closed end 310. The ramp 305 is initially inserted between two vertebral bodies upon which the links 406 may slide down (terminating at the closed end 310) for optimal placement. The links 406 comprise a groove 312 to allow the links 406 to slide on the ramp 305. The ramp 305 then becomes part of the permanent implant assembly 301. The links 406 are not connected to one another, thus gaps 311 exist until the links 406 come to rest next to one another. After insertion, the open end 309 may be appropriately bent or configured to prevent the links 406 from coming off of the ramp 305.

With respect to FIGS. 1(A) through 16(B), the apparatus 100 may be assembled as follows: the first, second, and third links 6, 8, 9 are assembled together in succession using hinge pins 7 to connect the first link 6 to the second link 8, and the second link 8 to the third link 9. Specifically, the connector mechanism 69 of the first link 6 is inserted between the pair of connector flanges 85 of the second link 8 such that the throughhole 65 of the connector mechanism 69 is aligned with each of the throughholes 120 of the pair of connector flanges 85. The flat side surfaces 68 of the connector mechanism 69 are dimensioned and configured to provide a frictional fit with the pair of connector flanges 85 of the second link 8 so the implant assembly 101 will not buckle or articulate prematurely upon impaction. Similarly, the pair of connector flanges 85 are dimensioned and configured to provide a frictional fit with the flat side surfaces 68 of the connector mechanism 69 so the implant assembly 101 will not buckle or articulate prematurely upon impaction. Once the throughholes 65, 120 are aligned, a hinge pin 7 is inserted therein to rotatably attach the first link 6 to the second link 8. The hinge pin 7 allows for a rotation axis of the first link 6 and the second link 8 during the insertion stages (shown in FIGS. 12(A) through 12(F)). After this, the connector mechanism 87 of the second link 8 is inserted between the pair of connector flanges 95 of the third link 9 such that the throughhole 121 of the connector mechanism 87 is aligned with each of the throughholes 130 of the pair of connector flanges 95. The flat side surfaces 124 of the connector mechanism 87 are dimensioned and configured to provide a frictional fit with the pair of connector flanges 95 of the third link 9 so the implant assembly 101 will not buckle or articulate prematurely upon impaction. Similarly, the pair of connector flanges 95 are dimensioned and configured to provide a frictional fit with the flat side surfaces 124 of the connector mechanism 87. Once the throughholes 121, 130 are aligned, a hinge pin 7 is inserted therein to rotatably attach the second link 8 to the third link 9.

Next, pivot peg 19 of the first hinged rod 2 is connected to pivot hole 31 of the second hinged rod 3. Then, pivot peg 35 of the second hinged rod 3 is connected to pivot hole 43 of the third hinged rod 4. After this, pivot peg 45 of the third hinged rod 4 is connected to pivot hole 54 of the insertion rod 5 and the assembled rods 2, 3, 4, 5 are inserted into the connected first, second, and third links 6, 8, 9. Finally, the retaining pin 1 is press fit into retention pin hole 66 of first link 6 and captures the retention hole 18 of the first hinged rod 2. More specifically, the exposed under surface 12 of retaining pin 1 is flush seated in retention pin hole 66 of first link 6. The second end 53 of the insertion rod 5 is adapted to be attached to an inserter tool/mechanism (not shown). Again, the insertion rod 5 does not get implanted in the vertebral body 200. Rather, the insertion rod 5 is removed once the implant assembly 101 is fully articulated in its final position.

The implant assembly 101 comprises various structural features, which provides it with enhanced functionality. For example, with respect to the first link 6, the serrated sides 61 provide friction and avoid dislocation after the assembly 101 is implanted in the vertebral body 200. Moreover, the tapered walls 63 allow for the structural distraction of adjacent vertebral bodies during insertion of the assembly 101 into the vertebral body 200. Additionally, the horizontal bone graft window 64 allows for bone packing prior to assembly 101 implantation in the vertebral body 200. Also, the rod retention hole 67 is adapted to accommodate the first hinged rod 2.

With respect to the second link 8, the serrated sides 88 provide friction and avoid dislocation after the assembly 101 is implanted in the vertebral body 200. Additionally, the horizontal bone graft window 123 allows for bone packing prior to assembly 101 implantation in the vertebral body 200. Also, the rod retention hole 89 is adapted to accommodate the first, second, and third hinged rods 2, 3, 4 during insertion of the connected rods 2, 3, 4, 5 during assembly of the apparatus 100. With respect to the third link 9, the serrated sides 98 provide friction and avoid dislocation after the assembly 101 is implanted in the vertebral body 200. Additionally, the horizontal bone graft window 132 allows for bone packing prior to assembly 101 implantation in the vertebral body 200. Also, the rod retention hole 97 is adapted to accommodate the first, second, and third hinged rods 2, 3, 4 and the insertion rod 5 during insertion of the connected rods 2, 3, 4, 5 during assembly of the apparatus 100. Moreover, the threaded hole 131 is adapted to connect with an inserter tool/mechanism (not shown) during implantation of the assembly 101 into a vertebral body 200. This connection is temporary as both the insertion rod 5 and the inserter tool/mechanism (not shown) are removed once the implant assembly 101 is fully articulated in its final position in the vertebral body 200. This is possible because the rod retention hole 97 is properly sized to allow release of the insertion rod 5 and the inserter tool/mechanism (not shown) once full articulation and final positioning of the assembly 101 is achieved in the vertebral body 200.

As mentioned, the implant assembly 101 is preferably attached to and inserted or impacted by insertion means such as an inserter tool/mechanism (not shown). In a preferred mode, the inserter tool/mechanism (not shown) may comprise of a shaft of an appropriate length. On one end may comprise a protrusion that is attached to the third link 9 via a thread, a snap fitting, or simply a friction fit stud. On the opposite end, the inserter tool/mechanism (not shown) may comprise a handle with an impact surface. The handle may also comprise a mechanism(s) to pull or push on the insertion rod 5 to articulate the implant assembly 101 during insertion into a vertebral body 200. When the implant-loaded inserter is lightly impacted, the implant assembly 101 is wedged between two vertebral bodies to slightly distract them (by means of tapered walls 63 of the first link 6) while being impacted with sufficient force to overcome the friction between the two bone surfaces.

As the implant assembly 101 is advanced into the spine, the surgeon may activate the mechanism(s) on the inserter tool/mechanism (not shown) to "bend" or articulate the implant assembly 101 until it is implanted in its final position (as shown in FIGS. 12(A) through 12(F)). Once the implant assembly 101 is fully articulated in its final position, the insertion rod 5 is allowed to disassemble from the implant assembly 101 by sliding the insertion rod 5 up or down towards the vertebral body 200. After the removal of the insertion rod 5, the inserter tool/mechanism (not shown) is also removed from the implant assembly 101.

FIG. 17, with reference to FIGS. 1(A) through 16(B), is a flow diagram illustrating a method of inserting an interbody spacer implant assembly 101 for interbody fusion into a vertebral body 200 according to an embodiment herein, wherein the method comprises connecting (501) an elongated connector mechanism (rods 2, 3, 4 or wire 205 or ramp 305 or flexible hinge 307) to a plurality of links (6, 8, 9, 306, 406); and inserting (503) the elongated connector mechanism (rods 2, 3, 4 or wire 205 or ramp 305 or flexible hinge 307) and the plurality of links (6, 8, 9, 306, 406) into the vertebral body 200, wherein specified ones of individual links 6, 8, 306, 406 of the plurality of links (6, 8, 9, 306, 406) are adapted to articulate individually with respect to other individual links 6, 8, 9, 306, 406 upon insertion into the vertebral body 200. The method may further comprise attaching an insertion rod 5 to the elongated connector mechanism (rods 2, 3, 4); using the insertion rod 5 to push the elongated connector mechanism (rods 2, 3, 4) and the plurality of links 6, 8, 9 into the vertebral body 200; and removing the insertion rod 5 from the elongated connector mechanism (rods 2, 3, 4) upon full insertion and final positioning of the elongated connector mechanism (rods 2, 3, 4) and the plurality of links 6, 8, 9 into the vertebral body 200.

The implant assembly 101 generally comprises a plurality of links 6, 8, 9 that are hinged together in one plane and at least one pivoting rod 2, 3, 4 (or some other connecting mechanism 205, 305, 307) assembled through the links 6, 8, 9 (or 306, 406) which are allowed to translate axially. These pivoting rods 2, 3, 4 (or some other connecting mechanism 205, 305, 307) function to pull or push on the hinged links 6, 8, 9 (or 306, 406) to articulate them into a desired shape during implantation. The pivoting rods 2, 3, 4 (or some other connecting mechanism 205, 305, 307) are configured to have a greater length-to-width ratio than the length-to-width ratio of each one of the individual links 6, 8, 9 (or 306, 406). The links 6, 8, 9 (or 306, 406) preferably only articulate one at a time sequentially, starting with the first link 6 and ending with the second link 8. More specifically, the third link 9 does not articulate; only the first link 6 and second link 8 articulate with reference to the third link 9 as shown in FIGS. 12(A) through 12(F). This constrained motion is due to the pivoting rods 2, 3, 4 (or some other connecting mechanism 205, 305, 307) only being able to articulate past the hinged link segments. The geometry of the pivoting rods 2, 3, 4 (or some other connecting mechanism 205, 305, 307) is constrained while inside the respective links 6, 8, 9 (or 306, 406) and cannot articulate until the previous link is in its fully articulated state. Once links 6, 8 (or 306) are fully articulated, only then can the insertion pivoting rod 2, 3, 4 (or some other connecting mechanism 205, 305, 307) be allowed to slide in the hinged portion (i.e., pivot peg 45) and dissemble from the implant assembly 101.

The embodiments herein may be utilized in surgery to stabilize the human spine. It may be used to replace a human disc that is no longer functioning properly and restore height between to vertebral bodies, or used to as a full or partial vertebral body replacement device. Preferably, the embodiments herein may be used with some form of the many available fixation devices either from a posterior, anterior, or lateral approach. Moreover, the embodiments herein provide an improvement over conventional devices in terms of the structure of the device, the method of implantation, and patient stability after implantation. The embodiments herein are dimensioned and configured to be manufactured from any appropriate implantable material(s) and may utilize all the standard surgical tools that accompany such devices.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A vertebral spacer implant comprising:
   a vertebral spacer body that is configured to interpose between two vertebra in a vertebral column;
   two connector flanges disposed on a surface of the vertebral spacer body;
   a connector mechanism receiving portion at least partially defined by the two connector flanges and the vertebral spacer body;
   a pivot element receiving throughhole defined by the two connector flanges;
   an insertion rod retention portion defined by the vertebral spacer body; and
   an insertion rod configured to engage the insertion rod retention portion, the insertion rod comprising a retention pin engaging retention hole configured to allow the insertion rod to apply a force to a vertebral spacer in either tension or compression,
   wherein:
      the two connector flanges are substantially parallel;
      the pivot element receiving throughhole defines a rotation axis substantially perpendicular to the two connector flanges; and
      the connector mechanism receiving portion is configured to allow the vertebral spacer body to pivot about the rotation axis.

2. The vertebral spacer implant of claim 1, further comprising a pivot element comprising:
   a connector mechanism; and
   an insertion tool connecting portion defined by the pivot element,
   wherein:
      the connector mechanism is configured to engage a connector mechanism receiving portion at least partially defined by two connector flanges of a vertebral spacer body;
      the insertion tool connecting portion is configured to releasably engage an insertion tool; and
      the vertebral spacer body is configured to rotate relative to the pivot element.

3. The vertebral spacer implant of claim 1, wherein the insertion rod is configured to prevent the vertebral spacer body from articulating relative to the pivot element during insertion into a vertebral column.

4. The vertebral spacer implant of claim 1, wherein the insertion rod is configured to actuate articulation of the vertebral spacer body relative to the pivot element.

5. The vertebral spacer implant of claim 1, further comprising a bone growth inducing material containing portion defined by the vertebral spacer body.

6. The vertebral spacer implant of claim 1, further comprising at least one bone friction inducing portion disposed on a surface of the vertebral spacer implant.

7. A vertebral spacer implant comprising:
a vertebral spacer body configured to interpose between two vertebra in a vertebral column, the vertebral spacer body comprising two substantially parallel connector flanges at least partially defining a connector mechanism receiving portion and a pivot element receiving throughhole;
an insertion tool connecting body, rotatably connected to the vertebral spacer body, comprising an insertion tool connecting portion defined by the insertion tool connecting body;
an insertion rod retention portion defined by the vertebral spacer body; and
an insertion rod configured to engage the insertion rod retention portion, the insertion rod comprising a retention pin engaging retention hole configured to allow the insertion rod to apply a force to a vertebral spacer in either tension or compression,
wherein the vertebral spacer body and insertion tool connecting body are configured to rotate relative to each other in a plane generally perpendicular to an axis defined by at least a portion of a vertebral column.

8. The vertebral spacer implant of claim 7, wherein the insertion rod is configured to prevent the vertebral spacer body from rotating relative to the insertion tool connecting body during insertion into a vertebral column.

9. The vertebral spacer implant of claim 7, wherein the insertion rod is configured to actuate the rotation of the vertebral spacer body relative to the insertion tool connecting body.

10. The vertebral spacer of claim 7, further comprising a bone growth inducing material containing portion defined by the vertebral spacer body.

11. The vertebral spacer implant of claim 7, further comprising at least one bone friction inducing portion disposed on a surface of the vertebral spacer implant.

12. A vertebral spacer implant comprising:
a spacer means for maintaining a separation between two vertebra in a vertebral column, the spacer means comprising two substantially parallel connector flanges at least partially defining a connector mechanism receiving portion and a pivot element receiving throughhole;
an insertion tool connecting means rotatably connected to the spacer means for releasably engaging an insertion tool; and
a rotation control means for controlling the rotation of the spacer means relative to the insertion tool connecting means, the rotation control means comprising a retention pin engaging retention means configured to allow the rotation control means to apply a force to a vertebral spacer in either tension or compression,
wherein the spacer means and insertion tool connecting means are configured to rotate relative to each other in a plane generally perpendicular to an axis defined by at least a portion of a vertebral column.

13. The vertebral spacer implant of claim 12, wherein the rotation control means is configured to prevent the spacer means from rotating relative to the insertion tool connecting means during insertion into a vertebral column.

14. The vertebral spacer implant of claim 12, wherein the rotation control means is configured to actuate the rotation of the spacer means relative to the insertion tool connecting means.

15. The vertebral spacer of claim 12, further comprising a bone growth inducing means defined by the spacer means for containing a bone growth inducing medium.

16. The vertebral spacer implant of claim 12, further comprising at least one bone friction inducing means disposed on a surface of the spacer means for inducing friction between the spacer means and a vertebra to hold the spacer means stationary in a vertebral column.

\* \* \* \* \*